(12) United States Patent  
Mayeaux

(10) Patent No.: US 9,018,608 B1
(45) Date of Patent: Apr. 28, 2015

(54) OPTICAL SENSOR FOR DETECTING LIQUID

(75) Inventor: Donald P Mayeaux, St Amant, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 920 days.

(21) Appl. No.: 13/186,437

(22) Filed: Jul. 19, 2011

Related U.S. Application Data

(63) Continuation-in-part of application No. 12/822,920, filed on Jun. 24, 2010, now Pat. No. 8,522,630.

(60) Provisional application No. 61/288,317, filed on Dec. 20, 2009, provisional application No. 61/476,294, filed on Apr. 17, 2011.

(51) Int. Cl.
G01N 15/06 (2006.01)
G01N 21/3577 (2014.01)

(52) U.S. Cl.
CPC .................. *G01N 21/3577* (2013.01)

(58) Field of Classification Search
CPC .............. G01N 35/08; G01N 2201/08; G01N 2201/0833; G01N 2201/061; G01N 2201/062; G01N 2201/06106; G01N 2201/06113; G01N 2201/0612
USPC ....... 250/573, 338.5, 357.1, 364, 428, 432 R, 250/434–438, 559.16, 564; 73/863; 356/436, 347, 441, 442; 359/226.3, 359/228
See application file for complete search history.

(56) References Cited

U.S. PATENT DOCUMENTS

| | | | | |
|---|---|---|---|---|
| 4,242,590 A * | 12/1980 | von Tluck | ...................... | 250/577 |
| 4,713,552 A * | 12/1987 | Denis et al. | .................... | 250/577 |
| 4,809,551 A * | 3/1989 | Grossiord | ........................ | 73/327 |
| 4,998,022 A * | 3/1991 | Tregay | ........................... | 250/577 |
| 5,088,324 A * | 2/1992 | Nemeth | .......................... | 73/291 |
| 5,106,580 A | 4/1992 | Mudiam | | |
| 5,381,022 A * | 1/1995 | Nemeth et al. | ................ | 250/577 |
| 6,661,504 B2 * | 12/2003 | Rakucewicz | .................. | 356/128 |
| 6,701,794 B2 | 3/2004 | Mayeaux | | |
| 6,827,486 B2 | 12/2004 | Welker | | |
| 6,964,517 B2 | 11/2005 | Welker | | |
| 7,472,615 B2 | 1/2009 | Mayeaux | | |
| 8,867,040 B2 * | 10/2014 | Pope et al. | ........................ | 356/437 |
| 2004/0232364 A1* | 11/2004 | Omatoi | ........................ | 250/577 |
| 2007/0225695 A1* | 9/2007 | Mayer et al. | .................... | 606/15 |

* cited by examiner

Primary Examiner — Georgia Y Epps
Assistant Examiner — Kevin Wyatt
(74) Attorney, Agent, or Firm — Joseph T Regard Ltd plc

(57) ABSTRACT

An optical liquid sensor utilizing a light source, fiber optic cables, a light detector and an irregular transparent surface is provided to detect the presence of liquid in mist and continuous form. The sensor may be integrated into a probe designed for insertion into a pressurized fluid process.

26 Claims, 4 Drawing Sheets

OPTICAL SENSOR FOR DETECTING LIQUID

The present application claims the benefit of Provisional Application 61/476,294, filed Apr. 17, 2011, and entitled "Optical Sensor for Detecting Liquid Mist and Continuous Liquid in a Pressurized System".

The present application also is a continuation in part of U.S. patent application Ser. No. 12/822,920, filed Jun. 24, 2010 now U.S. Pat. No. 8,522,630, and entitled "A System for Retrieving a Fluid Sample from a Fluid Sample Source", the contents of which are incorporated herein by reference thereto, which '920 application claims the benefit of U.S. Provisional Patent Application Ser. No. 61/288,317 filed Dec. 20, 2009.

TECHNICAL FIELD OF THE INVENTION

The present invention relates to an optical sensor system for detecting the presence of liquids. The system utilizes a unique transparent detector design which permits the passage of light through a roughed outer surface when no liquid is present, but upon liquid gathering on the roughened outer surface, said surface becomes reflective so as to reflect light to a sensor, indicating the presence of liquid. The preferred embodiment of the present invention relates to apparatus and method used to detect liquid mist and continuous liquids in a pressurized process gas. The process gas detected in the exemplary embodiment of the invention is natural gas and the fluid detected may be hydrocarbon, water, or other fluid, and the system will work equally well with other gases and/or liquids and/or environments.

BACKGROUND OF THE INVENTION

In the production, processing, transportation, and distribution of natural gas, it is very important to determine if liquid is present in any form. Hydrocarbon liquids entrained in the gas phase have a major impact on the value of natural gas. Gas turbines, which are utilized for driving gas compressors which move the gas in a pipeline, cannot tolerate liquid, even in mist form. Liquid separators in the natural gas pipeline, which remove entrained liquid, often spill over and cause problems downstream. Ensuring that the industry standards apply for the sampling of natural gas is another reason that is it important to know if liquid is present is present or not. API 14.1 and GPA 2166 industry standards state that said standards do not apply if there is liquid present in the natural gas pipeline.

Hydrocarbon mist has the same physical and chemical properties as a continuous hydrocarbon liquid phase. Therefore, hydrocarbon mist can seriously impact the value of natural gas and cause problems in the pipeline by enhancing corrosion and forming hydrates. Spillover of absorbing liquid from absorbers designed to remove H2S and/or water vapor can also cause many problems in the pipeline. The ability to detect any form of liquid is very important to assess the value of the natural gas and to the safety of pipeline operation.

The following is a list of U.S. patent numbers which rely on differences in the refractive indices of fluids for detecting liquids in continuous form: U.S. Pat. Nos. 4,713,552; 6,801,678; and 6,363,784. Other U.S. patents depend on a fluid fluorescing in order to detect it, such as U.S. Pat. Nos. 4,942,306 and 4,870,292. The present invention does not rely on refractive indices or fluorescing in order to detect any liquid in various forms such as droplets, mist, or in continuous form.

GENERAL SUMMARY OF INVENTION

The present invention provides a relatively simple, robust, and effective apparatus and method of detecting the presence of fluid or fluid droplets in mist form in process gas or the like. The preferred embodiment of the present invention includes a light source configured to transmit light through a first fiber optic cable, which conveys the light the base of a cone-shaped, transparent body having a rough or abraded exterior, angled surface.

When said exterior surface is dry, light projected therethrough is scattered and diffused, due to the surface imperfections formed thereon. When said exterior surface becomes wet, liquid fills the voids in the surface imperfections formed on the exterior surface, rendering said surface reflective, so as to cause light projected therein to be reflected into a second fiber optic cable, which cable conveys said light to a light detector, which outputs a signal when light is detected. This signal can be utilized in a number of ways, including sounding an alarm. A bifurcated fiber optic cable may be utilized instead of two individual fiber optic cables in the present case, one for sending light into the transparent body, one for receiving the reflected light therefrom.

While the preferred, exemplary embodiment of the present invention teaches that the detector body is cone-shaped, said configuration is not intended to be limiting, and it is envisioned that other configurations would likewise work in a satisfactory manner. Projecting the light from within the transparent body has the advantage that no working parts are exposed to the harsh environment which is being monitored. The cone shape does have its advantages, including the potential to detect liquid 360 degrees about the axis of the cone.

Nonetheless, an alternative detection device might be fashioned wherein light is simply projected through air upon an abraded or roughened surface, so that, when said surface receives liquid, specular reflection of the light reflects same to a detector. While this alternative design might not be particularly suitable for use in detecting liquid in a hydrocarbon fluid stream, it is envisioned as useful in other applications.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

Figure 1:
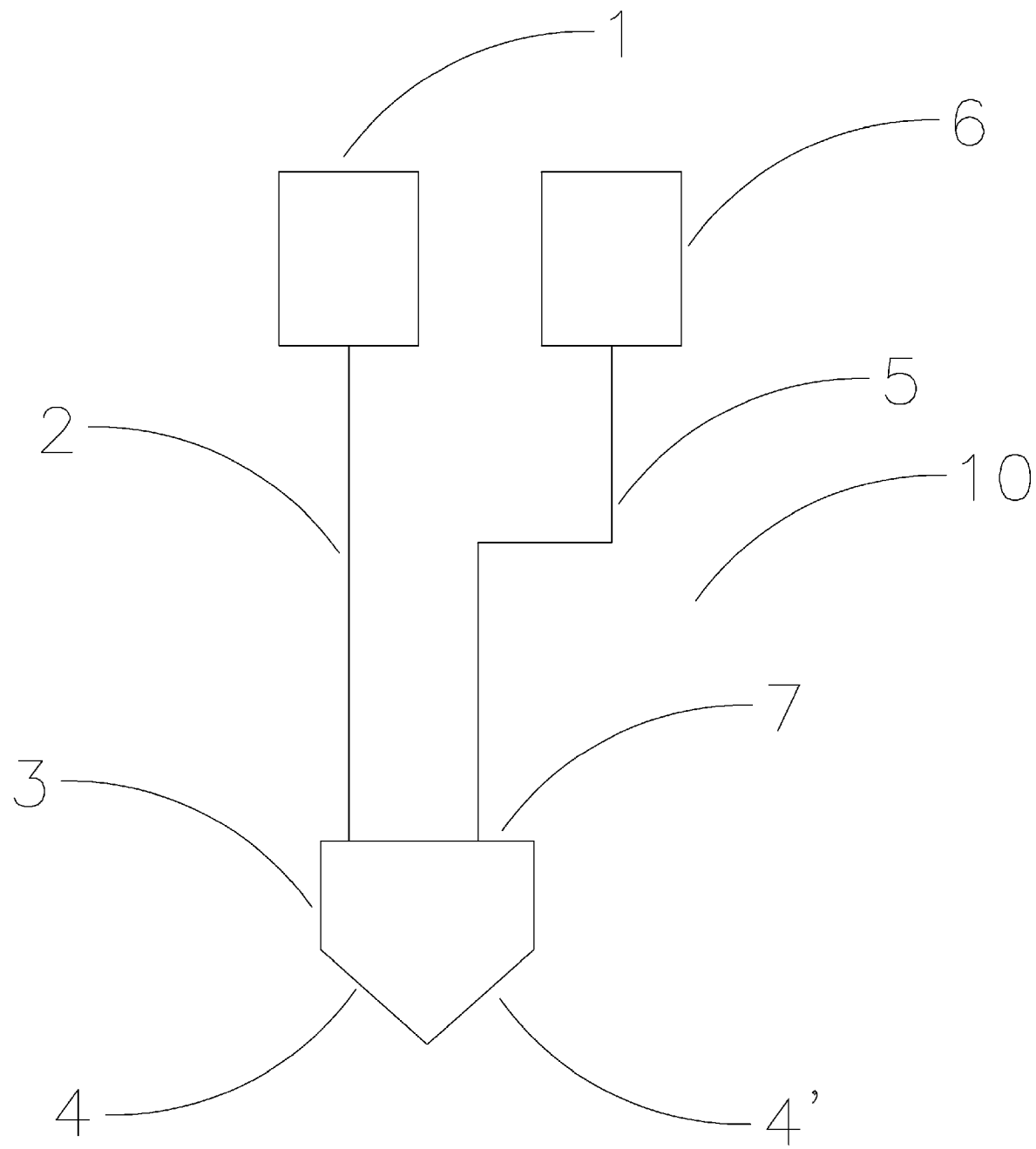
FIG. 1 is a schematic diagram of an exemplary embodiment of the liquid detection system of the present invention.
Figure 2:
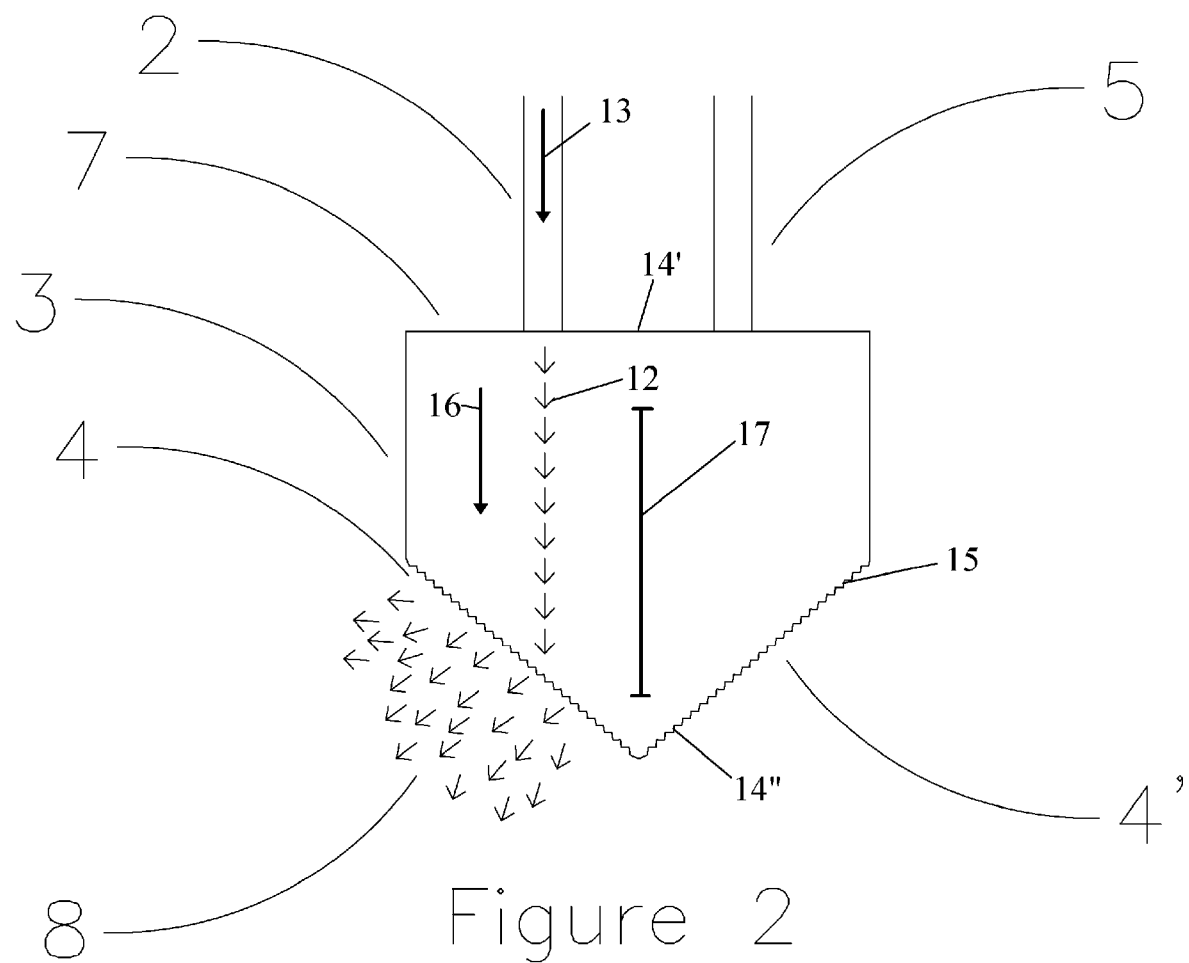
FIG. 2 is a side, cross-sectional view of the liquid detection system of FIG. 1, illustrating a transparent cone with its roughed exterior surface dry, with light being scattered.

Referring to FIGS. 1 and 2, a light source 1 (such as, for example, an LED light, laser or incandescent light bulb) is provided to convey 13 light 12, utilizing fiber optic cable 2, to a light permeable transport body 3. The transport body 3 is preferably formed of, for example, glass, acrylic, polycarbonate, or other light permeable, non-diffusing material, and is shown having a conical configuration, forming base 14' (which may be circular or polygonal) and apex 14", wherein the axis 17 is at a right angle with regard to the base. Said transport body 3 is configured so light 12 passes into upper surface 7 (at the base 14'), then through transport body 3 to surface 15.

Because a smooth surface can be specular reflective, surface 15 is roughened, for example with 120 grit sandpaper, etching, or other process to form a roughed surface 4, 4' such that less than 50% of the light is diffuse reflected, so that when the roughed surface 4 is dry, said light 12 is scattered and dispersed 8 with minimal internal reflection.

Conversely, when liquid 21, 21' such as water or oil gathers roughed surfaces 4 and 4', the voids in the roughed surface 4, 4' are filled to provide a relatively smooth, light reflective surface 22 (See FIGS. 1 and 3), so that said light 12 is reflected 9 from reflective surface 22 to now reflective surface 22', which reflects said light (via its angle) through upper surface 7 into fiber optic cable 5 wherein said light is conveyed to light detector 6.

Figure 4:
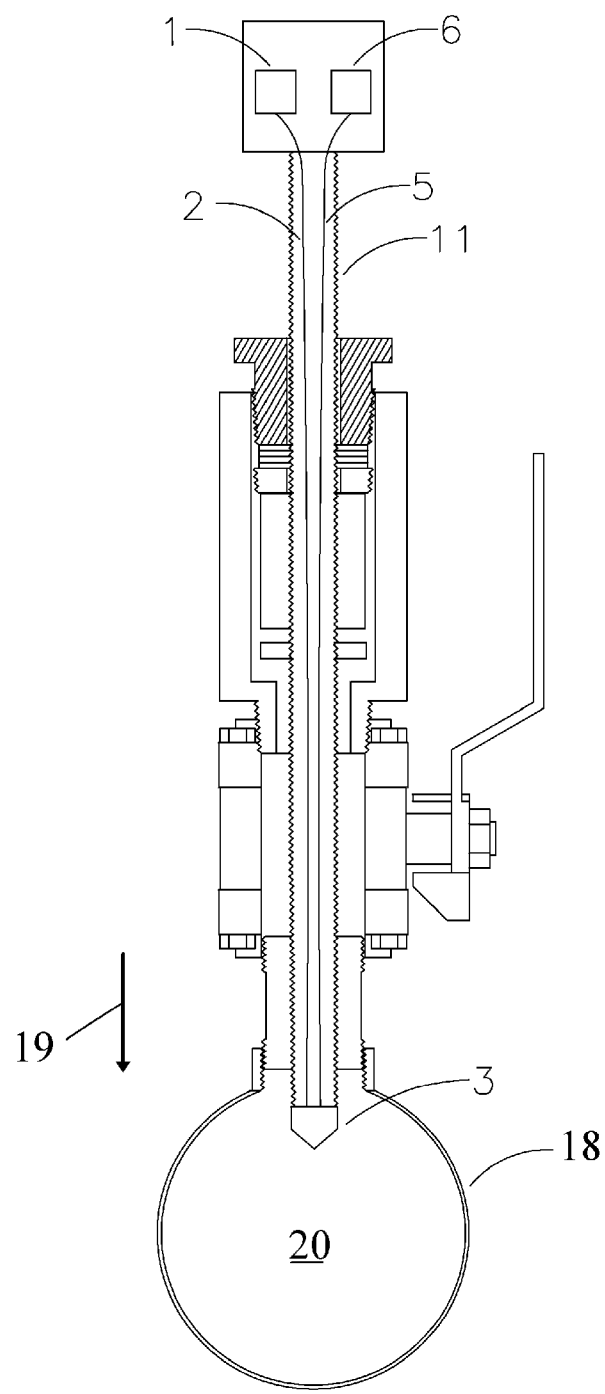
FIG. 4 is a partially cut-away view the liquid detection system of FIG. 1 integrated into a probe, shown configured for insertion into a pressurized system.

Light detector 6, upon detecting said light, is configured to output an electrical signal, which can be utilized to convey that surface 4 and 4' are wet. Liquid detection system 10 may be integrated into a probe 11 (FIG. 4), suitable for insertion into a pressurized vessel or pipeline.

Continuing with FIGS. 1-4, upon insertion 19 into a pipeline 18, the body 3 is dry and the light source 1 is initiated. As long as the process gas 20 passing through the pipeline 18 (such as natural gas) is dry, no alarm will sound, as the light 12 is diffused/scattered and dispersed, with minimal internal reflection. But if liquid droplets or mist result in liquid accumulating on roughed surfaces 4, 4', at some point light reflective surfaces 22, 22' are formed, at which point the light 12 is reflected in the manner shown in FIG. 3 to the fiber optic cable 5 for detection via light detector.

Figure 3:
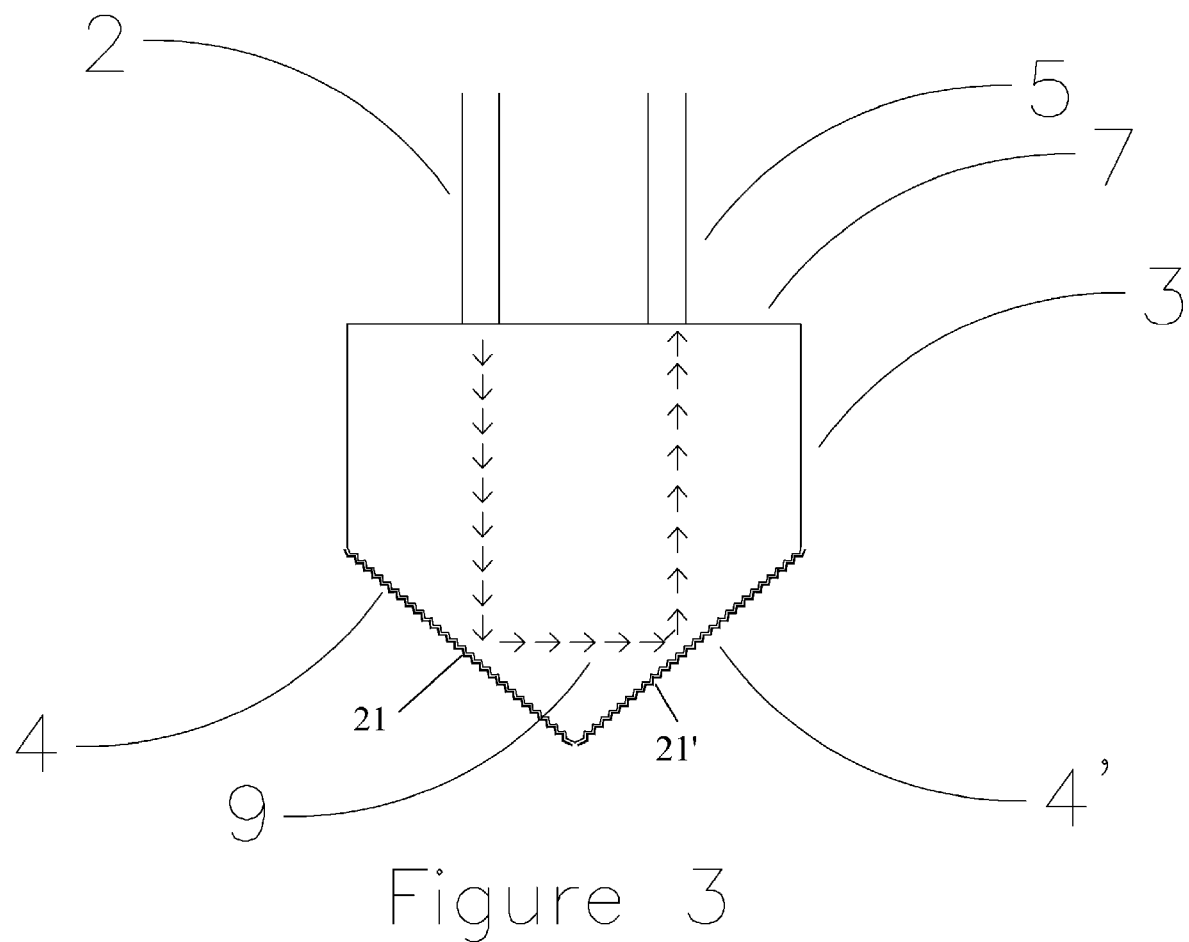
FIG. 3 is a side, cross-sectional view of the cone of FIG. 2, illustrating said transparent cone with its roughed surfaces, this time wet, resulting in said light being reflected internally.

While the example of FIG. 3 illustrates opposing roughed surfaces 4, 4' along opposing sides of the cone, an alternative embodiment of the present invention would require only one of surfaces 4, 4' to be roughed or otherwise irregular, as a smooth surface would reflect light, with or without liquid thereupon.

In another embodiment, the light detector (or fiber optic cable therefrom) could be positioned in or on body 3 to receive the reflection from roughed surface 4 directly, without having to rely upon a secondary reflection such as surface 4' shown in FIG. 3.

While the present invention is shown using internal reflection (projection and reflection within transparent body 3), it is noted that a similar system may be provided wherein the beam of light is projected directly to an externally roughed surface, which can be positioned to reflect light to an external detector upon becoming reflective due to the accumulation of liquid thereupon via the phenomenon of specular reflection.

Use of the present system in detecting a liquid may comprise for example, the steps of:
a. Providing a light source, a first fiber optic cable and a second fiber optic cable, a transparent cone with an irregular surface, and a light detector;
b. Positioning said first fiber optic cable in a manner so as to convey light from said light source to said irregular surface;
c. Initiating said light source, providing light;
d. Utilizing said first fiber optic cable to convey said light through said transparent cone to said rough surface;
e. Utilizing said irregular surface of said transparent cone as a light diffuser to scatter or disperse said light so as to provide minimal internal reflection;
f. Allowing liquid to accumulate on said irregular surface, engaging same so as to transform said irregular surface from a light diffuser to a light reflector;
g. allowing said light reflector to reflect said light from said first fiber optic cable so as to be received by said second fiber optic cable;
h. allowing said second fiber optic cable to convey said light to said light detector;
i. Upon said light detector detecting light, utilizing said light detector to generate an electrical signal.

LISTING OF ELEMENTS

\# Description
1. Light source
2. Fiber optic cable transmitting light source to cone
3. Body
4.' Roughed surfaces
5. Fiber optic cable transmitting reflected light to light detector
6. Light detector
7. Upper surface
8. Diffused or scattered light
9. Internal reflected light
10. Liquid detection system
11. Probe
12. light
13. conveyed
14','' base, apex
15. angled surface
16. through
17. Axis
18. Pipe
19. Insertion
20. gas
21.' Fluid
22. 22' Reflective surface

EXEMPLARY SPECIFICATION

Body 3 formed of polycarbonate.
Body configuration is a right circular cone.
Light 13 is an LED, while Light detector 6 is a photocell. The Light 13 and 6 in the present working embodiment of the invention is provided by Panasonic, Model #505-C2.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A liquid detector, for detecting liquid particles in a gas stream, comprising:
    a transparent cone having a base, an apex and an outer surface, said outer surface having a diffusion surface to diffuse light passing therethrough;
    a light source formed to transmit a beam of light into said base of said cone, said beam of light passing through said cone to said outer surface of said cone such that, in the absence of liquid, said beam of light is diffused by said diffusion surface;
    a light detector formed so as to detect light reflecting from said outer surface of said cone;
    whereby, upon liquid particles engaging said diffusion surface of said cone, said liquid particles collect at said diffusion surface to provide a specular reflecting surface, so as to reflect light from said light source to said light detector.

2. The liquid detector of claim 1, wherein a first fiber optic cable is situated between said light source and said base of said cone.

3. The liquid detector of claim 2, wherein a second fiber optic cable is situated between said base of said cone and said light detector.

4. The liquid detector of claim 3, wherein said light source comprises an LED.

5. The liquid detector of claim 3, wherein said light source comprises a laser.

6. The liquid detector of claim 3, wherein said cone comprises a base, an apex, and an axis therebetween, wherein said axis is situated at a right angle relative said base.

7. The liquid detector of claim 6, wherein said base of said cone is radial.

8. The liquid detector of claim 6, wherein said base of said cone is polygonal.

9. The liquid detector of claim 1, wherein there is further provided a probe configured for insertion into said gas stream, and wherein said transparent cone is mounted to said probe.

10. The liquid detector of claim 1, wherein said diffusion surface comprises irregularities formed in said outer surface of said cone.

11. The liquid detector of claim 1, wherein said diffusion surface is abraded.

12. The liquid detector of claim 1, wherein said diffusion surface is etched.

13. A method for detection of liquid, comprising the steps of:
   a. Providing a light source, a first fiber optic cable and a second fiber optic cable, a transparent cone with an irregular surface, and a light detector;
   b. Positioning said first fiber optic cable in a manner so as to convey light from said light source to said irregular surface;
   c. Initiating said light source, providing light;
   d. Utilizing said first fiber optic cable to convey said light through said transparent cone to said irregular surface;
   e. Utilizing said irregular surface of said transparent cone as a light diffuser to scatter or disperse said light at said surface of said cone so as to provide minimal internal reflection;
   f. Allowing liquid to accumulate on said irregular surface, engaging same so as to transform said irregular surface from a light diffuser to a light reflector;
   g. allowing said light reflector to reflect said light from said first fiber optic cable so as to be received by said second fiber optic cable;
   h. allowing said second fiber optic cable to convey said light to said light detector;
   I. Upon said light detector detecting light, utilizing said light detector to generate an electrical signal.

14. The method of claim 13, wherein there is provided after step "I." the additional step "j." of utilizing said electrical signal to generate an alarm.

15. The method of claim 10, wherein there is provided after step "e" the additional step "e1" of mounting said transparent cone to a probe; and "e2" of utilizing said probe to insert said transparent cone into a pressurized system.

16. The method of claim 15, wherein in step "E2" said pressurized system comprises a flow of gas having entrained fluid therein, and wherein there is provided the additional step "f" of allowing said liquid particles to accumulate at said irregular surface, providing said liquid to engage same so as to transform said irregular surface from a light diffuser to a light reflector.

17. The method of claim 16, wherein step "f" includes the sub-step "f1" of allowing said liquid particles to fill-in said irregular surface to provide spectral reflectivity, providing a light reflector.

18. The method of detecting a liquid, comprising the steps of:
   a. providing a body formed of transparent material having a detection surface, said detection surface having surface irregularities so as to diffuse the projection of light thereupon;
   b. placing said detection surface in a monitoring area comprising a gas flow having entrained liquid therein;
   c. allowing said liquid to collect on said detection surface, providing collected liquid, said collected liquid engaging said irregularities thereon to provide a specular reflective surface;
   d. illuminating said detection surface with a light beam;
   e. allowing said specular reflective surface to reflect said light beam, providing a reflected light beam; and
   f. sensing said reflected light beam.

19. The method of claim 18, wherein in step "c" said collected liquid engages said irregularities on said detection surface to transform said detection surface from a light diffuser to a light reflector.

20. The method of claim 19, wherein after step "a.", there is provided the further step "a1" of providing a light source formed to project a beam of light into said transparent body, at said detection surface, and in step "d.", said light source is used to generate said light beam.

21. The method of claim 20, following step "a1" there is further provided step "a2" of providing a light detector associated with said transparent body, said light detector positioned to detect light reflected from said reflective surface, and in step "f.", said light detector is used to sense said reflected light beam.

22. The method of claim 21, wherein in step "a." said transparent body comprises a cone having a base and an apex, with an outer sidewall therebetween, and wherein said detection surface is formed on said outer sidewall.

23. The method of claim 22, wherein in step "d", there is further provided the step of using a fiber optic cable to convey said light beam from said light source to said transparent body.

24. The method of claim 23, wherein in step "f", there is further provided the step of using a fiber optic cable to convey said reflected light beam from said transparent body to a light detector.

25. The method of claim 24, wherein the step of forming irregularities in said detection surface further comprises the step "a(i)" of abrading said detection surface with an abrasive so as to diffuse at least 50% of light directed thereto.

26. The method of claim 21, where step "b." further comprises the sub-steps of:
   b.(1) mounting said transparent body to a probe; and
   b.(2) inserting said probe into a pressurized system.

* * * * *